United States Patent
Lee et al.

(10) Patent No.: US 11,383,085 B2
(45) Date of Patent: Jul. 12, 2022

(54) ELECTRICAL STIMULATION APPARATUS AND METHOD FOR CONTROLLING SAME

(71) Applicant: Y-BRAIN INC., Daejeon (KR)

(72) Inventors: Ki Won Lee, Seongnam-si (KR); Jong Min Jang, Suwon-si (KR); Byung Gik Kim, Daegu (KR)

(73) Assignee: Y-BRAIN INC., Daejeon (KR)

( * ) Notice: Subject to any disclaimer, the term of this patent is extended or adjusted under 35 U.S.C. 154(b) by 203 days.

(21) Appl. No.: 16/398,936

(22) Filed: Apr. 30, 2019

(65) Prior Publication Data

US 2019/0255327 A1    Aug. 22, 2019

Related U.S. Application Data

(63) Continuation of application No. PCT/KR2016/012363, filed on Oct. 31, 2016.

(51) Int. Cl.
*A61N 1/04* (2006.01)
*A61N 1/36* (2006.01)
*A61N 1/08* (2006.01)
*A61B 5/00* (2006.01)
*A61B 5/291* (2021.01)

(52) U.S. Cl.
CPC .......... *A61N 1/36021* (2013.01); *A61B 5/00* (2013.01); *A61N 1/04* (2013.01); *A61N 1/0484* (2013.01); *A61N 1/0492* (2013.01); *A61N 1/08* (2013.01); *A61N 1/36* (2013.01); *A61N 1/36025* (2013.01); *A61B 5/291* (2021.01); *A61B 5/6803* (2013.01); *A61N 1/0456* (2013.01)

(58) Field of Classification Search
CPC ................ A61N 1/0484; A61N 1/0492; A61N 1/36025; A61N 1/0456
See application file for complete search history.

(56) References Cited

U.S. PATENT DOCUMENTS

| | | | | |
|---|---|---|---|---|
| 6,423,193 B1 * | 7/2002 | Miller | ................... | C25B 11/073 204/242 |
| 8,700,164 B2 | 4/2014 | DeGiorgio et al. | | |
| 10,342,969 B2 * | 7/2019 | Lee | ........................ | A61N 1/0484 |
| 10,413,725 B2 * | 9/2019 | Lee | ........................ | A61N 1/3603 |

(Continued)

FOREIGN PATENT DOCUMENTS

| | | |
|---|---|---|
| KR | 10-1525450 B1 | 6/2015 |
| KR | 10-1539654 B1 | 7/2015 |
| KR | 10-1540273 B1 | 7/2015 |

OTHER PUBLICATIONS

English translation of KR 10-1539654 (Year: 2015).*

(Continued)

*Primary Examiner* — Eric D. Bertram
(74) *Attorney, Agent, or Firm* — Studebaker & Brackett PC

(57) ABSTRACT

An electrical stimulation apparatus is provided. The electrical stimulation apparatus includes a frame worn on a user, an electrode module including a plurality of microelectrodes covered by a single patch, one surface of the electrode module is connected to the frame and the other surface faces the user while being covered by the single patch, and a processor controlling an operation of the electrode module such that a target effect is capable of being provided to the user through electrical stimulation in a state where the frame is worn on the user.

19 Claims, 12 Drawing Sheets

(56) References Cited

U.S. PATENT DOCUMENTS

| | | | |
|---|---|---|---|
| 2004/0158298 A1* | 8/2004 | Gliner | A61N 1/36021 |
| | | | 607/48 |
| 2010/0152810 A1* | 6/2010 | Minogue | A61N 1/36014 |
| | | | 607/48 |
| 2011/0220505 A1* | 9/2011 | Wang | B01L 3/502792 |
| | | | 204/547 |
| 2011/0288610 A1 | 11/2011 | Brocke | |
| 2015/0051663 A1 | 2/2015 | Hagedorn | |
| 2015/0238762 A1 | 8/2015 | Pal et al. | |
| 2016/0150992 A1* | 6/2016 | Lee | A61B 5/291 |
| | | | 600/544 |

OTHER PUBLICATIONS

International Search Report issued in PCT/KR2016/012363; dated Aug. 18, 2017.

The extended European search report issued by the European Patent Office dated Oct. 22, 2019, which corresponds to European Patent Application No. 16920204.1-1124 and is related to U.S. Appl. No. 16/398,936.

* cited by examiner

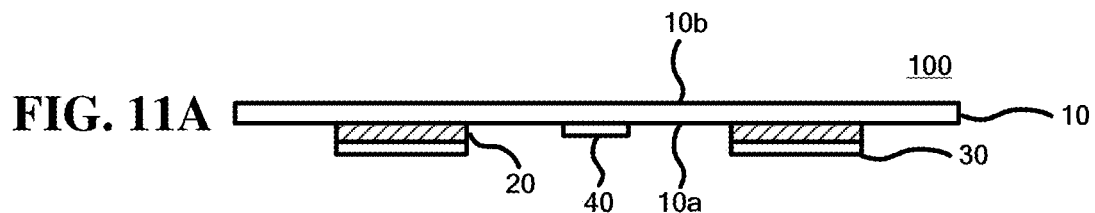
FIG. 11A
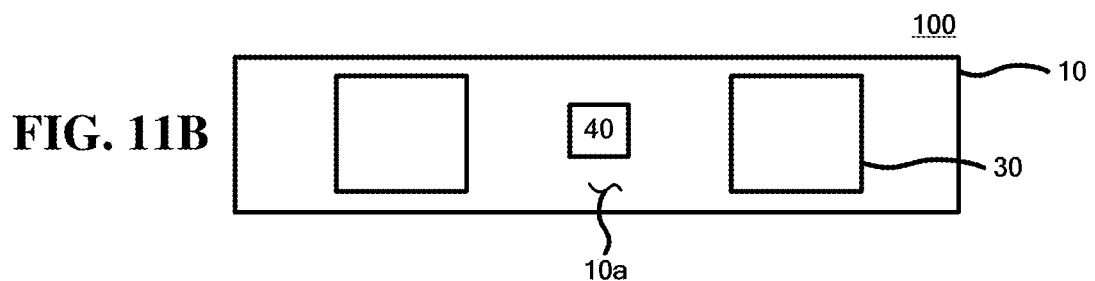
FIG. 11B
FIG. 12
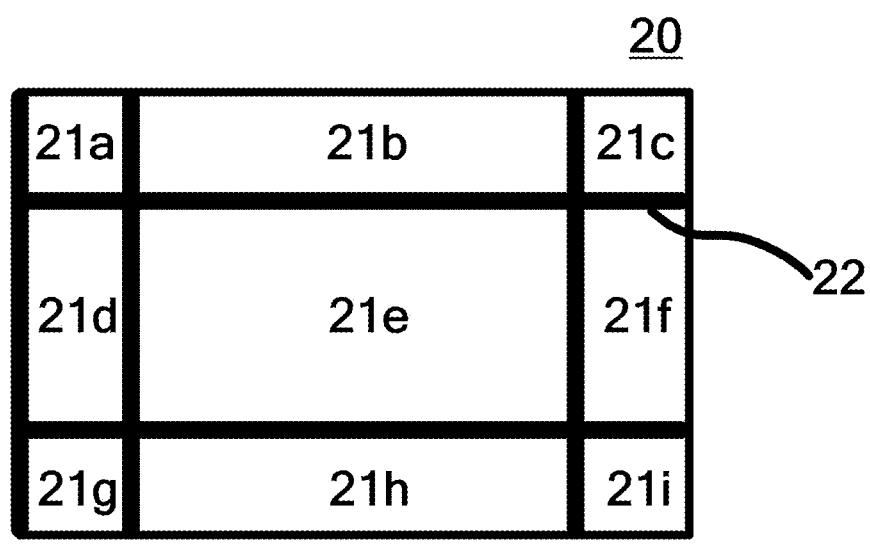

ELECTRICAL STIMULATION APPARATUS AND METHOD FOR CONTROLLING SAME

CROSS-REFERENCE TO RELATED APPLICATIONS

The present application is a continuation of International Patent Application No. PCT/KR2016/012363, filed on Oct. 31, 2016. The disclosure of the above-listed application is hereby incorporated by reference herein in their entirety.

BACKGROUND

Embodiments of the inventive concept described herein relate to an electrical stimulation apparatus that applies transcranial current stimulation (tCS) to a user, and a method for controlling the same.

The technology of brain electrical stimulation using transcranial electrical stimulation may be known to be effective in improving cognitive ability and treating mental illnesses such as depression and Attention Deficit Hyperactivity Disorder (ADHD).

In particular, two types of electrical stimulation methods are used for transcranial electrical stimulation.

First, there is a method in which a doctor directly attaches an electrode to a location where electrical stimulation is required, on the head of an examinee (user) and then applies transcranial electrical stimulation to the location. When such the electrical stimulation apparatus is used, because the doctor directly attaches an electrode to a location where electrical stimulation is required, it is possible to accurately apply the electrical stimulation to the target region. On the other hand, because non-medical professionals do not know exactly the location where electrical stimulation is required, it is difficult for the non-medical professionals to use this electrical stimulation method. Furthermore, even though medical professionals use the electrical stimulation method, the medical professionals need to set the electrical stimulation apparatus every time whenever using the electrical stimulation apparatus, it is troublesome for the medical professionals to use the electrical stimulation method.

In addition, the electrical stimulation apparatus with a helmet or hat shape surrounding the entire head may be used. A plurality of electrodes may be uniformly distributed in the electrical stimulation apparatus. That is, because the electrodes are positioned in advance on the electrical stimulation apparatus, the electrical stimulation may be possible only when the examinee wears the electrical stimulation apparatus. As such, the method may reduce the preparation time for electrical stimulation and may increase convenience. However, because examinees have different head shapes, it is difficult to accurately perform the electrical stimulation, when a standardized electrical stimulation apparatus is mounted and then electrical stimulation is performed.

SUMMARY

Embodiments of the inventive concept provide an electrical stimulation apparatus that controls the operation of an electrode module such that a user is capable of being provided with a target effect via electrical stimulation while the user wears an electrical stimulation apparatus, and a method for controlling the same.

The technical problems to be solved by the present inventive concept are not limited to the aforementioned problems, and any other technical problems not mentioned herein will be clearly understood from the following description by those skilled in the art to which the inventive concept pertains.

According to an exemplary embodiment, an electrical stimulation apparatus includes a frame worn on a user, an electrode module including a plurality of microelectrodes covered by a single patch, and a processor controlling an operation of the electrode module such that a target effect is capable of being provided to the user through electrical stimulation in a state where the frame is worn on the user. One surface of the electrode module is connected to the frame and the other surface faces the user while being covered by the single patch.

According to another exemplary embodiment, an electrical stimulation apparatus includes a frame worn on a user, an electrode module including a plurality of microelectrodes covered by a single patch, and a processor controlling an operation of the electrode module such that a stimulation center of the electrode module is capable of being adjusted in a state where the frame is worn on the user. One surface of the electrode module is connected to the frame and the other surface faces the user while being covered by the single patch.

According to another exemplary embodiment, an electrical stimulation apparatus includes a frame worn on a user, an electrode module including a plurality of microelectrodes covered by a single patch, and a processor controlling an operation of the electrode module such that a stimulation center of the electrode module is capable of being adjusted in a state where the frame is worn on the user. One surface of the electrode module is connected to the frame and the other surface faces the user while being covered by the single patch.

According to another exemplary embodiment, an electrical stimulation apparatus includes a frame worn on a user, and an electrode module including a plurality of microelectrodes covered by a single patch. One surface of the electrode module is connected to the frame and the other surface faces the user while being covered by the single patch. Each of the plurality of microelectrodes includes a microelectrode surface. A size of one microelectrode surface of the plurality of microelectrode surfaces is different from a size of another microelectrode surface of the plurality of microelectrode surfaces.

According to another exemplary embodiment, an electrical stimulation apparatus includes a frame worn on a user and an electrode module including a plurality of microelectrodes covered by a single patch. One surface of the electrode module is connected to the frame and the other surface faces the user while being covered by the single patch. Density of a microelectrode positioned in a center area of the electrode module is different from density of a microelectrode positioned in an outer area of the electrode module.

According to another exemplary embodiment, a method of controlling an electrical stimulation apparatus in a state where the electrical stimulation apparatus including a frame worn on a user, an electrode module including a plurality of microelectrodes and connected to the frame, and a patch, one surface of which covers the plurality of microelectrodes of the electrode module and the other surface of which contacts the user, is worn on the user includes grasping the state where the electrical stimulation apparatus is worn on the user and controlling an operation of the electrode module such that a target effect is capable of being provided to the user through electrical stimulation in a state where the frame is worn on the user, based on the grasped result.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIGS. 11A and 11B are drawings illustrating a schematic configuration of an electrical stimulation apparatus, according to the second embodiment of the inventive concept;

FIG. 12 illustrates an electrode module of an electrical stimulation apparatus, according to the third embodiment of the inventive concept;

Figure 14:
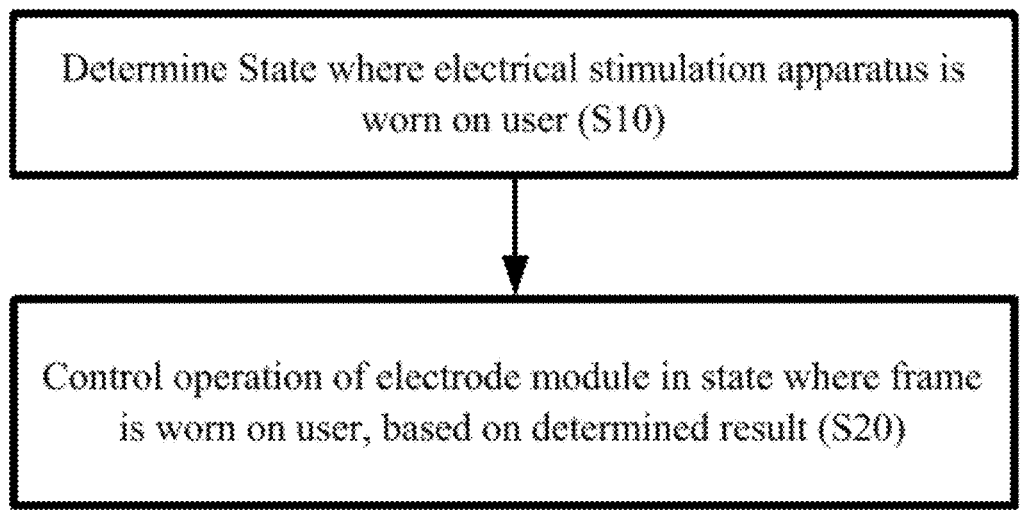
Figure 15:
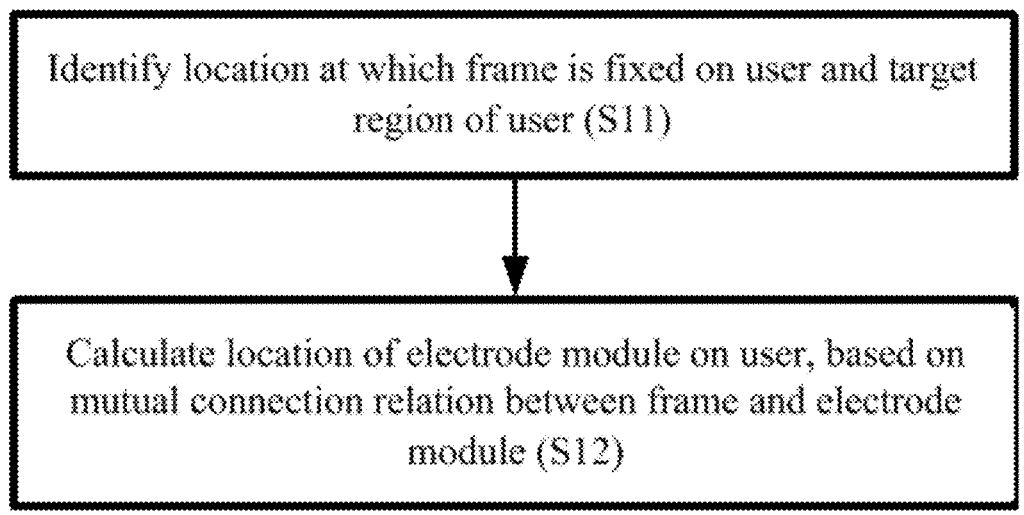
Figure 16:
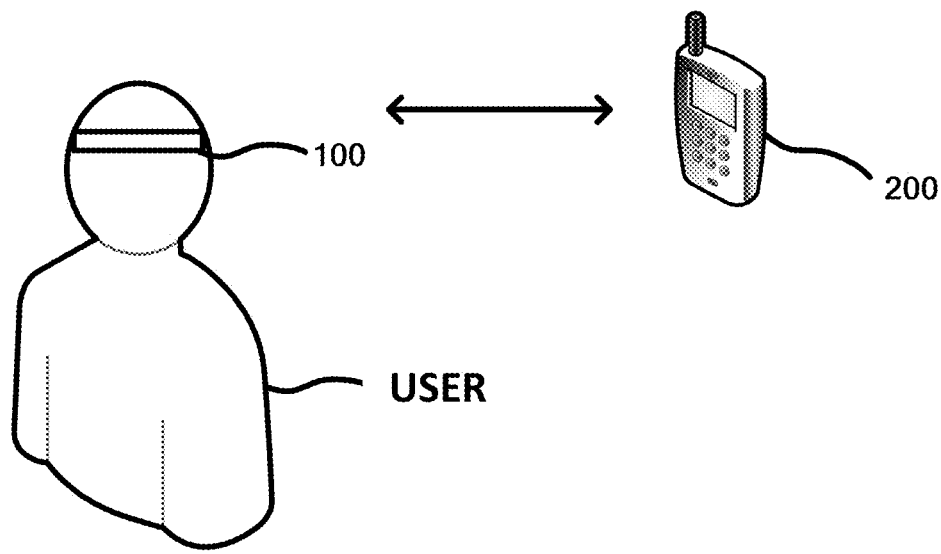
Figure 17:
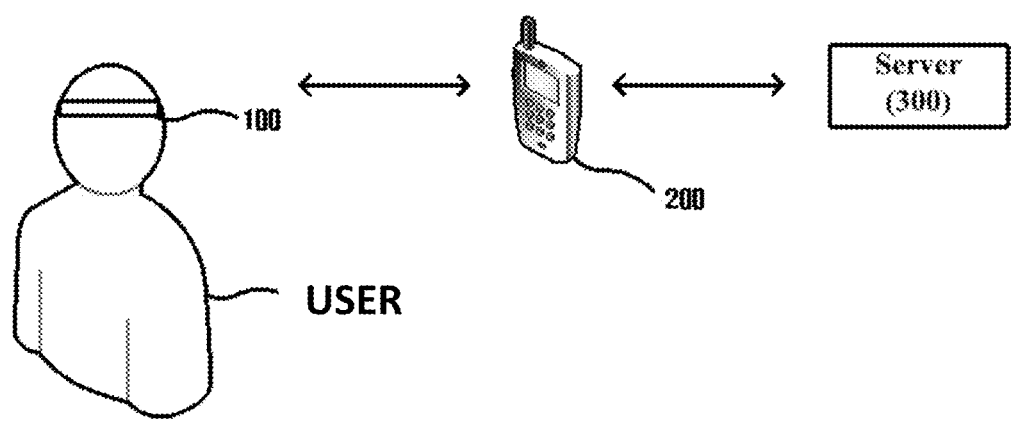

13A to 13D illustrate views for describing an operation of an electrical stimulation apparatus, according to the third embodiment of the inventive concept;

FIG. 14 is a flowchart of a method for controlling an electrical stimulation apparatus, according to the first embodiment of the inventive concept;

FIG. 15 is a flowchart of operation S10 in FIG. 14;

FIG. 16 is a view for describing an execution subject of a method for controlling an electrical stimulation apparatus, according to the first embodiment of the inventive concept; and FIG. 17 is a view for describing an execution subject of a method for controlling an electrical stimulation apparatus, according to the second embodiment of the inventive concept.

DETAILED DESCRIPTION

Advantage points and features of the inventive concept and a method of accomplishing thereof will become apparent from the following description with reference to the following figures, wherein embodiments will be described in detail with reference to the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the concept of the inventive concept to those skilled in the art. The inventive concept may be defined by scope of the claims. Meanwhile, the terminology used herein to describe embodiments of the inventive concept is not intended to limit the scope of the inventive concept.

The terminology used herein is for the purpose of describing embodiments and is not intended to limit the inventive concept. As used herein, the singular terms are intended to include the plural forms as well, unless the context clearly indicates otherwise. The terms "comprises" and/or "comprising" used herein does not exclude presence or addition of one or more other elements, in addition to the aforementioned elements. The same reference numerals denote the same elements throughout the specification. As used herein, the term "and/or" includes any and all combinations of one or more of the associated components. It will be understood that, although the terms "first", "second", etc., may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

As illustrated in the figures, spatially relative terms, such as "below", "beneath", "lower", "above", "upper", and the like, may be used herein for ease of description to describe the relationship between one component and other components. It will be understood that the spatially relative terms are intended to encompass different orientations of the components in use or operation in addition to the orientation depicted in the figures. For example, when inverting a component shown in the figures, a component described as "below" or "beneath" of another component may be placed "above" another element. Thus, the exemplary term "below" may include both downward and upward directions. The components may also be oriented in different directions, and thus the spatially relative terms may be interpreted depending on orientation.

Hereinafter, embodiments about an electrical stimulation apparatus of the inventive concept will be described in detail with reference to accompanying drawings.

The electrical stimulation apparatus according to an embodiment of the inventive concept may be a device that applies transcranial electrical stimulation to a user, and the transcranial electrical stimulation may be transcranial direct current stimulation (tDCS) or transcranial alternating current stimulation (tACS). However, the inventive concept is not limited thereto.

An electrical stimulation apparatus 100 according to the first embodiment of the inventive concept will be described with reference to FIGS. 1 to 10.

Figure 1:
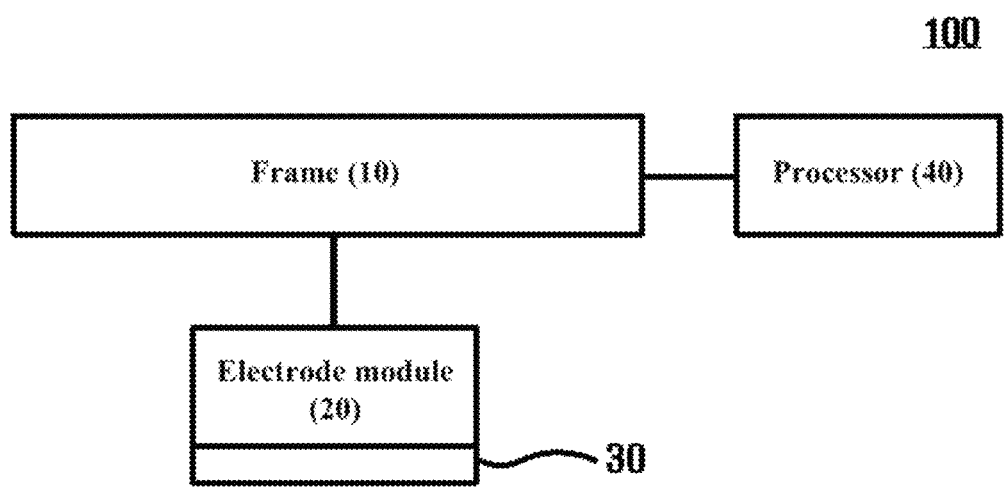
FIG. 1 is a drawing illustrating a schematic configuration of an electrical stimulation apparatus, according to the first embodiment of the inventive concept.
Figure 2:
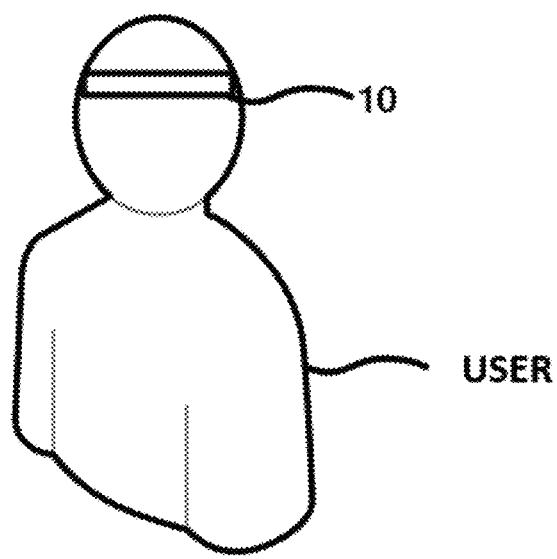
FIG. 2 is a view in which a user wears an electrical stimulation apparatus, according to the first embodiment of the inventive concept.
Figure 3:
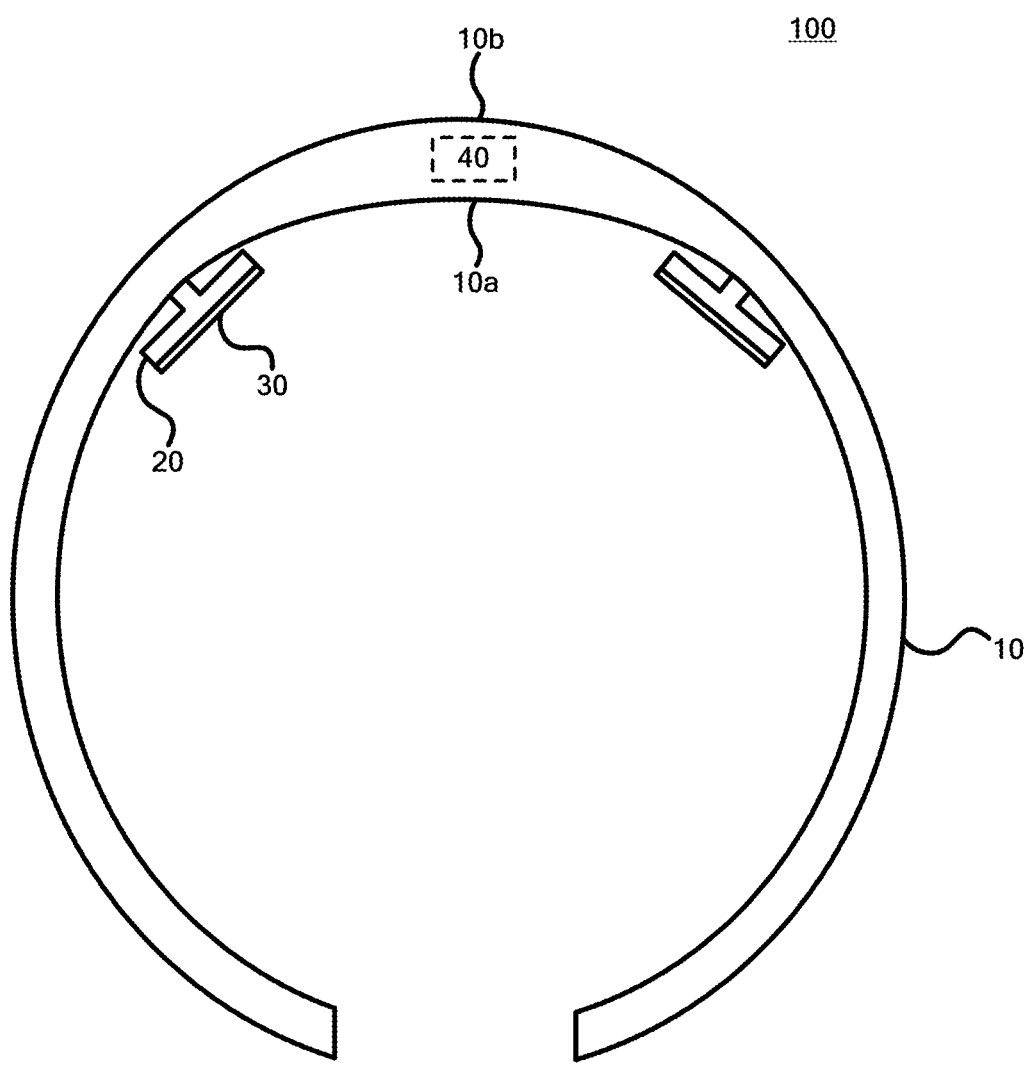
FIG. 3 is an exemplary view of an electrical stimulation apparatus, according to the first embodiment of the inventive concept.
Figure 4:
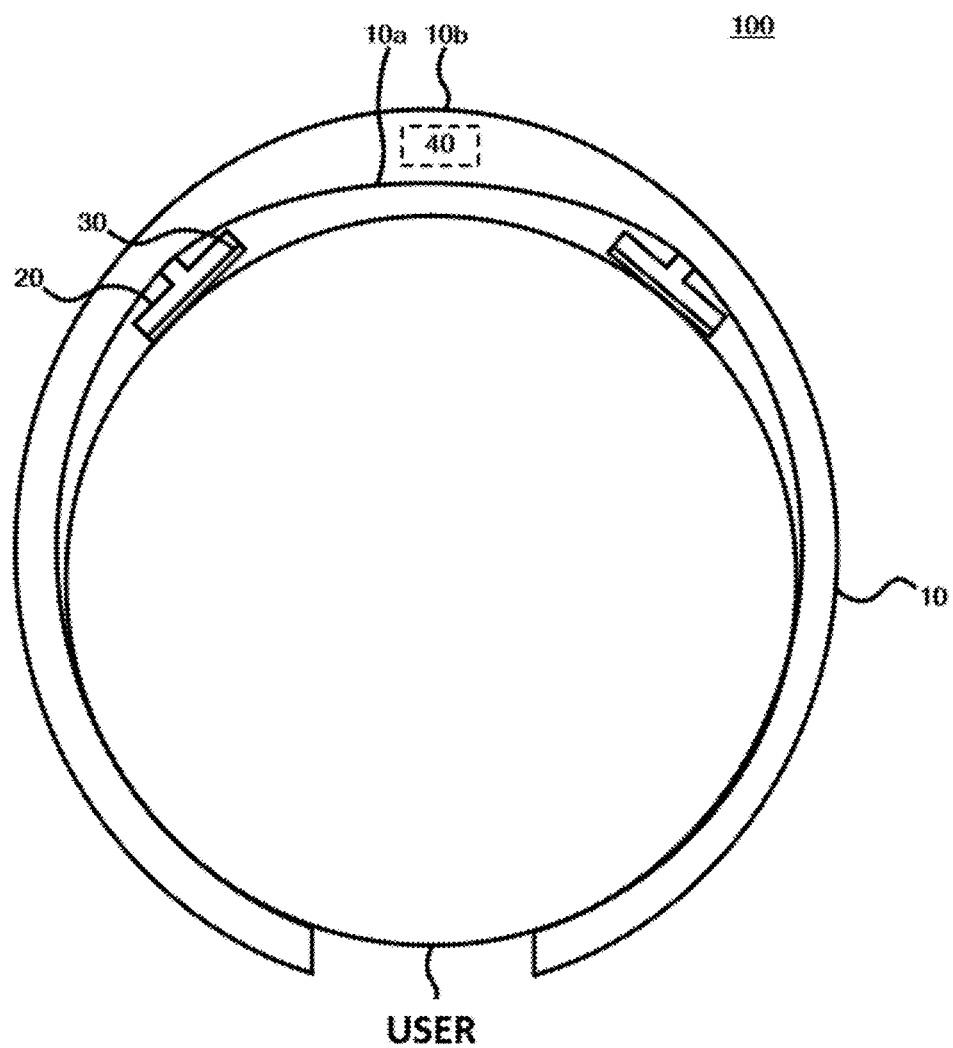
FIG. 4 is a view in which a user wears an electrical stimulation apparatus of FIG. 3.
Figure 5:
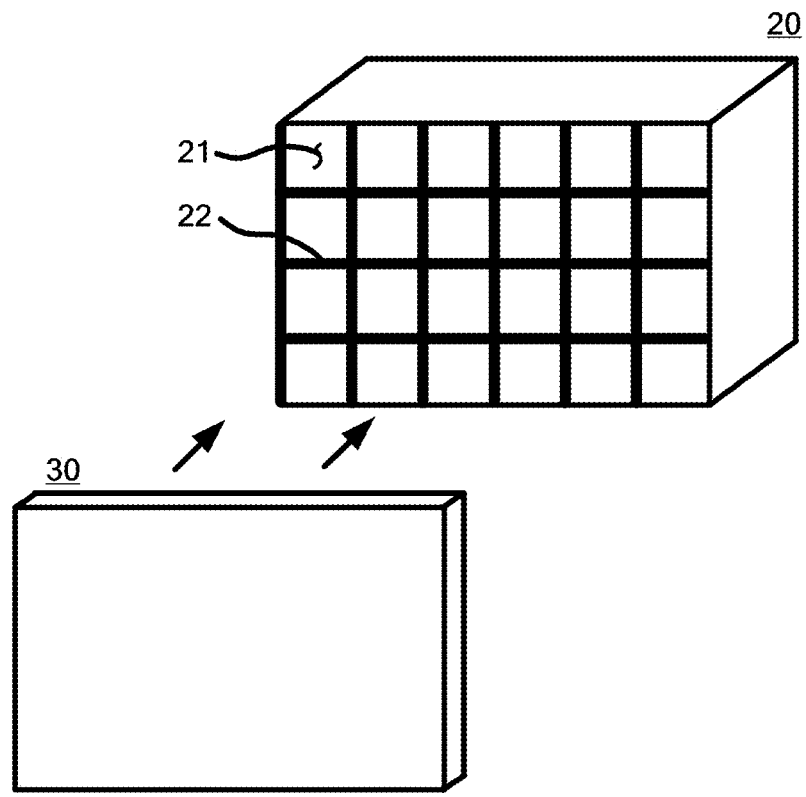
FIG. 5 is a view illustrating an electrode surface of an electrode module of FIG. 1.
Figure 6:
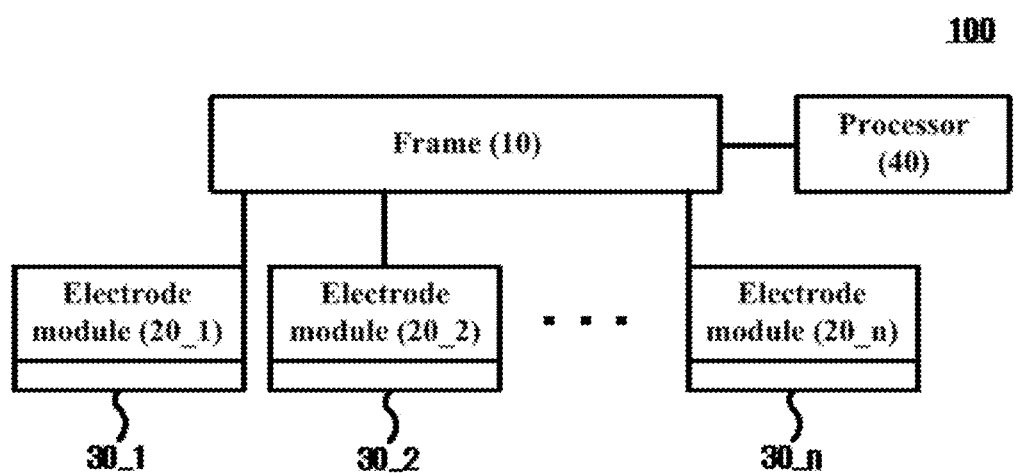
FIG. 6 is a diagram of an electrical stimulation apparatus including a plurality of electrode modules, according to some embodiments.
Figure 7:
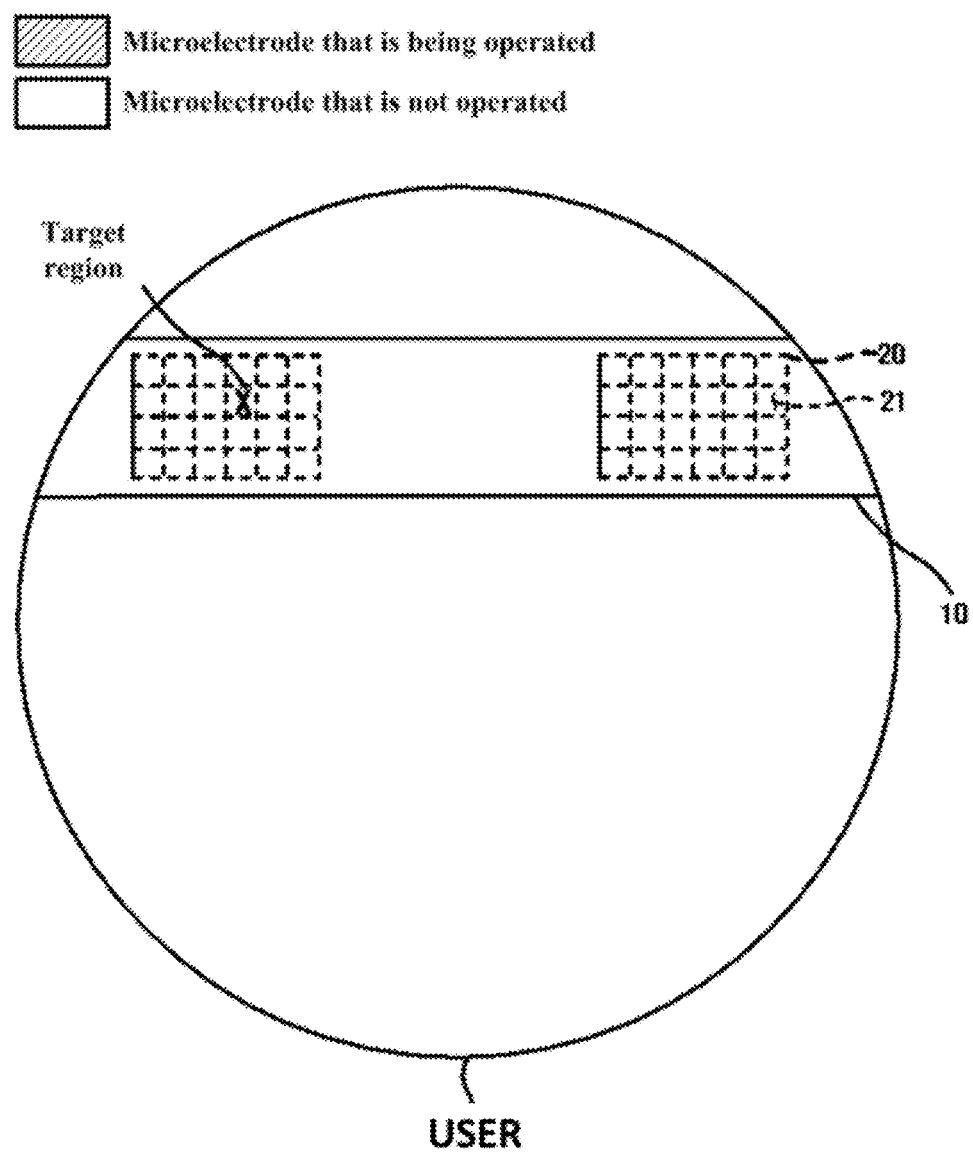
FIGS. 7 to 9 are views for describing adjustment of an electrical stimulation location or an electrical stimulation area of an electrical stimulation apparatus, according to the first embodiment of the inventive concept.
Figure 8:
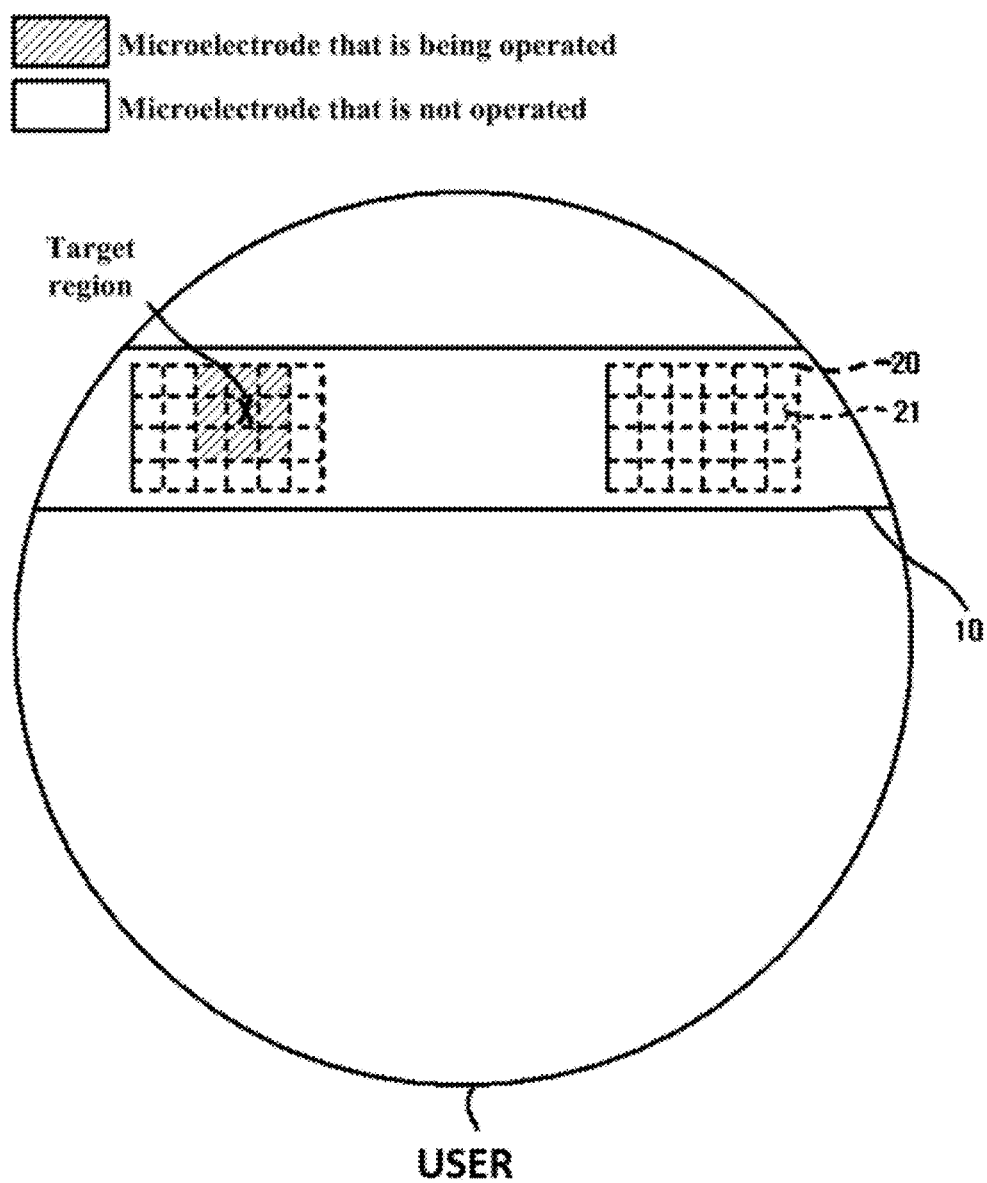
Figure 9:
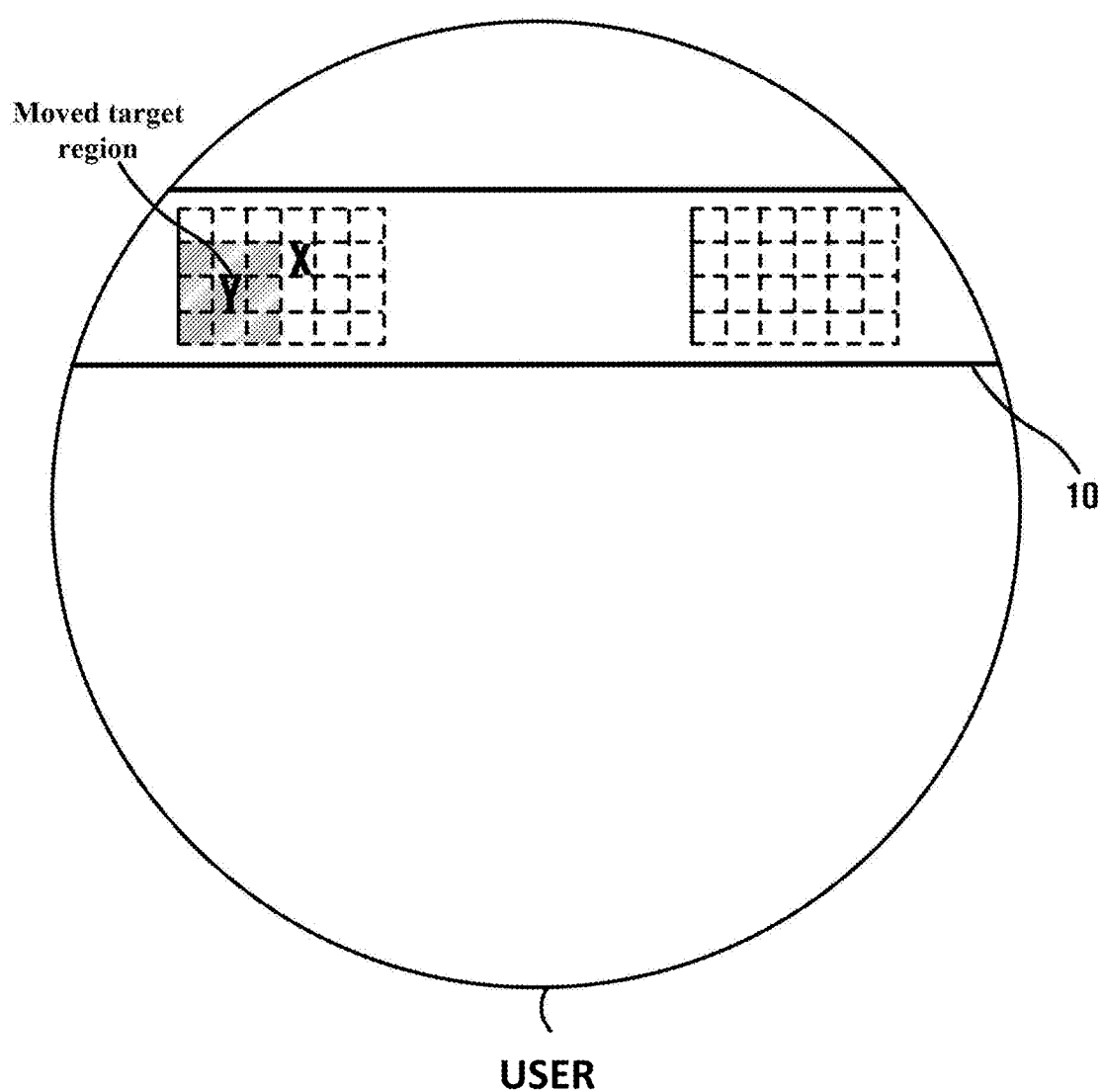
Figure 10:
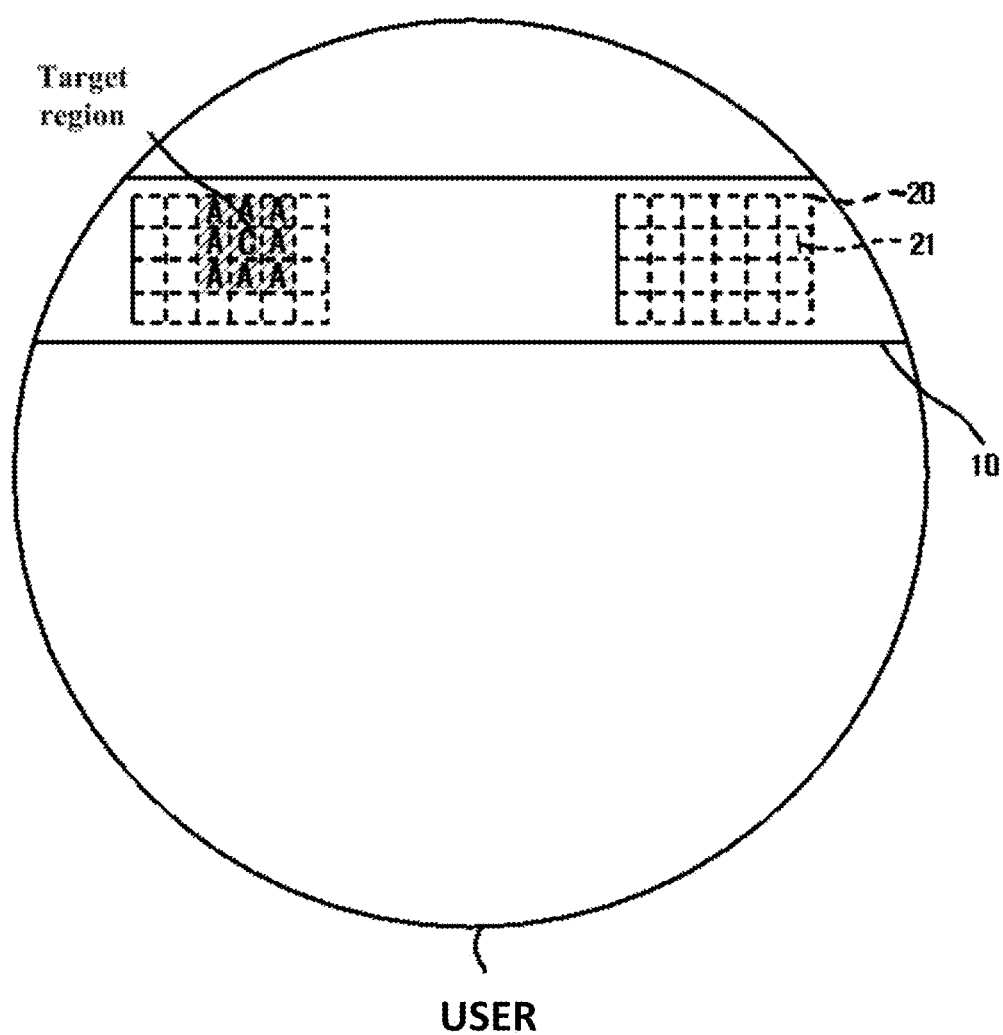
FIG. 10 is a view for describing adjustment of electrical stimulation density of an electrical stimulation apparatus, according to the first embodiment of the inventive concept.
Figure 13A:
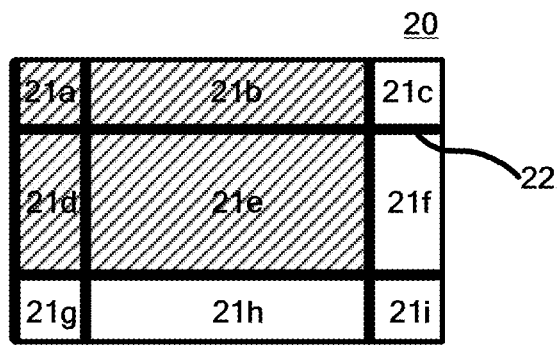
Figure 13B:
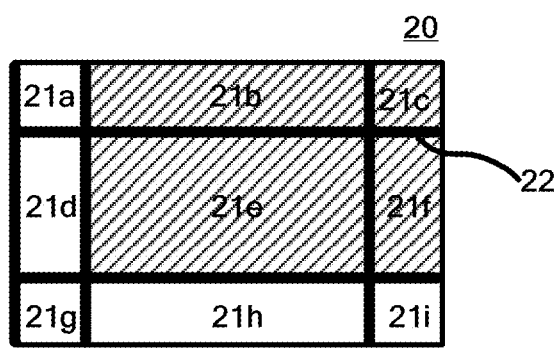
Figure 13C:
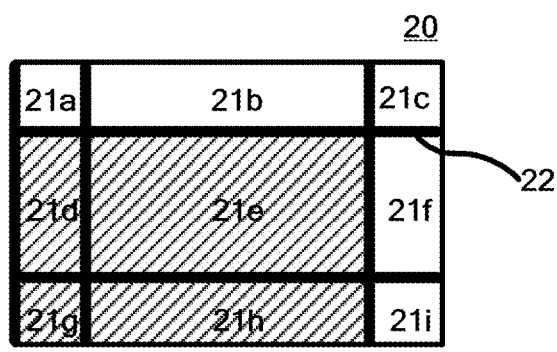
Figure 13D:
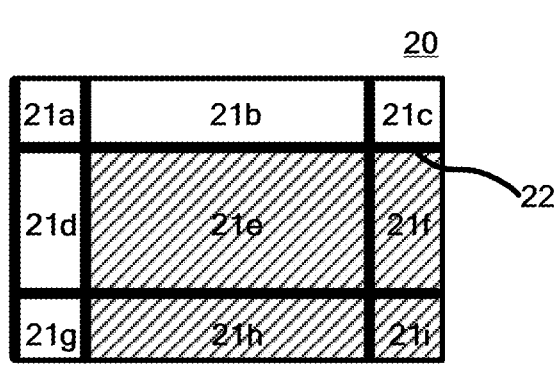

Referring to FIG. 1, the drawing illustrating a schematic configuration of the electrical stimulation apparatus 100 according to the first embodiment of the inventive concept is illustrated. Referring to FIG. 2, a view in which a user wears the electrical stimulation apparatus 100 according to the first embodiment of the inventive concept is illustrated. Referring to FIG. 3, an exemplary view of the electrical stimulation apparatus 100 according to the first embodiment of the inventive concept is illustrated. Referring to FIG. 4, a view in which a user wears the electrical stimulation apparatus 100 of FIG. 3 is illustrated. Referring to FIG. 5, a view illustrating an electrode surface of an electrode module 20 of FIG. 1 is illustrated. Referring to FIG. 6, a diagram of the electrical stimulation apparatus 100 including the plurality of electrode modules 20 according to some embodiments is illustrated. Referring to FIGS. 7 to 9, views for describing the adjustment of an electrical stimulation location or an electrical stimulation area of the electrical stimulation apparatus 100 is disclosed. Referring to FIG. 10, a view for describing the adjustment of the electrical stimulation density of the electrical stimulation apparatus 100 according to the first embodiment of the inventive concept is disclosed.

Referring to FIG. 1, the electrical stimulation apparatus 100 according to the inventive concept may include a frame 10, the electrode module 20, a patch 30, and a processor 40. However, the configuration of the electrical stimulation apparatus 100 is not limited thereto. In some embodiments, the electrical stimulation apparatus 100 may include more or fewer components than the components illustrated in FIG. 1.

Above all, the frame 10 will be described. The frame 10 may be worn on a user. In particular, referring to FIG. 2, the frame 10 may be worn on the user, and the location of the frame 10 may be fixed. As the user wears the frame 10, the electrical stimulation apparatus 100 may apply electrical stimulation to the user while the location is fixed on the user.

The frame 10 may be the frame of the electrical stimulation apparatus 100. For example, various components such as the electrode module 20, the processor 40, and a current source (not illustrated) may be connected to the frame 10 or may be embedded in the frame 10. However, the inventive concept is not limited thereto.

In particular, the frame 10 may be connected to the electrode module 20, and the relative connection relation between the frame 10 and the electrode module 20 may be fixed. That is, the connection angle or connection location associated with how the electrode module 20 is connected to the frame 10 may be determined in advance. Accordingly, in the case where the user wears the electrical stimulation apparatus 100 according to the inventive concept, when the user grasps where the frame 10 is fixed on the user, where the electrode module 20 is positioned on the user, or where the electrode module 20 contacts on the user may be determined using the relative connection relation between the frame 10 and the electrode module 20.

The relative connection relation between the frame 10 and the electrode module 20 may vary depending on which target effect the apparatus 100 provides to the user. Herein, the target effect may be, for example, the treatment of specific mental illnesses as the effect to be obtained through the electrical stimulation of the electrical stimulation apparatus 100. However, the inventive concept is not limited thereto. For example, in the case of the electrical stimulation apparatus 100 for the treatment of Alzheimer's disease and the electrical stimulation apparatus 100 for the treatment of depression, the relative connection relation between the frame 10 and the electrode module 20 may be different. Because the scalp location where electrical stimulation is required to treat Alzheimer's disease and the scalp location where electrical stimulation is required to treat depression may be different from each other, the relative connection relation between the frame 10 and the electrode module 20 may vary depending on the difference in target effect.

Referring to FIGS. 3 and 4, one embodiment of the frame 10 will be described. The frame 10 may include a first surface 10a facing the user's head and a second surface 10b positioned opposite to the first surface 10a. Moreover, the frame 10 may have a shape capable of being worn on the user's head and may be worn and fixed to the user, due to the structural features of the frame 10. For example, the frame 10 may have a ring structure, one side of which is opened. However, the inventive concept is not limited thereto.

Because the frame 10 compresses the head due to the structural features of the frame 10 when the frame 10 is worn on the user's head, the frame 10 may be stably fixed to the user's head without falling downward by gravity. In some embodiments, the partial area of the frame 10 may be supported on the user's auricle such that the frame 10 may be stably worn on the user's head. However, in the case of the frame 10 of the shape capable of being worn on the head due to the structural feature, the shape of the frame 10 is not limited thereto.

In the meantime, referring to FIG. 4, because the relative connection relation between the frame 10 and the electrode module 20 is determined in advance in the electrical stimulation apparatus 100 according to an embodiment of the inventive concept, when where the frame 10 is fixed on the user is grasped, where the electrode module 20 is positioned on the user, or where the electrode module 20 contacts on the user may be estimated using the relative connection relation between the frame 10 and the electrode module 20.

Next, the electrode module 20 will be described. Referring to FIG. 5, the electrode module 20 may include a plurality of microelectrodes 21, and the plurality of microelectrodes 21 may be covered by the single patch 30. FIG. 5 illustrates an electrode surface on which the electrode module 20 contacts the patch 30. The electrode module 20 is divided into at least two or more microelectrodes 21. The microelectrodes 21 are used to indicate that the electrode of the electrode module 20 is divided into a plurality of electrodes.

In particular, the plurality of microelectrodes 21 included in the single electrode module 20 may be located adjacent to each other, and thus may form a single electrode array or a single group. However, each of the microelectrodes 21 may be electrically isolated from each other and may be individually (or independently) controlled by the processor 40. To this end, the surface of the microelectrode 21 included in each of the plurality of microelectrodes 21 may be electrically isolated by, for example, a non-conductive material 22 such as non-conductive silicon, or the like. However, the inventive concept is not limited thereto.

Herein, the electrode module 20 may be uniformly divided such that the plurality of microelectrodes 21 may be arranged uniformly. However, the inventive concept is not limited thereto. An embodiment in which the plurality of microelectrodes 21 are arranged nonuniformly will be described later.

In accordance with the electrical stimulation apparatus 100 according to an embodiment of the inventive concept, because the single electrode module 20 includes the plurality of microelectrodes 21, the electric stimulation may be applied to the area, in which the electrical stimulation has been applied using a single electrode, using the plurality of microelectrodes 21. As such, in accordance with the electrical stimulation apparatus 100 according to an embodiment of the inventive concept, it is possible to precisely control the stimulation location and to adjust the electrical stimulation density by adjusting the polarities of the plurality of microelectrodes 21, because the electrical stimulation is performed on a smaller area as a base unit.

In the meantime, referring to FIGS. 1 and 4, because one surface of the electrode module 20 is connected to the frame 10, and the other surface faces a user while being covered by the single patch 30, the electrode module 20 may receive current from a current source (not illustrated) and then may supply the current to the patch 30. Herein, the single electrode module 20 may become a reference unit for stimulating a single target region of a user. However, it may be possible to precisely control the single electrode module 20, using the plurality of microelectrodes 21.

That is, the single electrode module 20 may be covered by the single patch 30. As such, the fact that the plurality of microelectrodes 21 are covered by the single patch 30 may mean that the single electrode module 20 becomes the reference unit for stimulating a single target region of the user. Accordingly, the electrode module 20 according to an embodiment of the inventive concept may include the plurality of microelectrodes 21. However, considering that such the electrode module 20 is covered by the single patch 30, the function of the electrode module 20 according to an embodiment of the inventive concept may be different from the union of a plurality of electrodes for stimulating different target regions.

In addition, the electrode surface of the electrode module 20 covered by the single patch 30 may have a size great then the size of the electrode surface of the electrode of a conventional electrical stimulation apparatus 100. However, the inventive concept is not limited thereto. For example, assuming that the reference size of the conventional electrical stimulation is 30 mm×30 mm, the size of the conventional electrode surface or conventional patch 30 may be 30 mm×30 mm. In this case, the electrode surface size of the electrode module 20 included in the electrical stimulation apparatus 100 may be 50 mm×50 mm greater than 30 mm×30 mm that is the reference electrical stimulation. As such, the size of the patch 30 included in the electrical stimulation apparatus 100 according to an embodiment of the inventive concept may be 50 mm×50 mm greater than 30 mm×30 mm that is the reference electrical stimulation. However, the inventive concept is not limited thereto.

As such, in accordance with the electrical stimulation apparatus 100 according to an embodiment of the inventive concept, because the electrode surface size of the electrode module 20 is greater than the size of the reference electrical stimulation and the electrode module 20 includes the plurality of microelectrodes 21 capable of being controlled individually, it may be possible to adjust the electrical stimulation location such that the target effect is capable of being provided to the user through electrical stimulation in a state where the frame 10 is worn on a user. This will be described later.

In the meantime, the electrode module 20 may be connected to the frame 10 depending on the relative connection relation between the frame 10 and the electrode module 20. The electrical stimulation apparatus 100 illustrated in FIG. 1 may be illustrated as including the single electrode module 20, and the electrical stimulation apparatus 100 illustrated in FIG. 3 may be illustrated as including the two electrode modules 20. Further, as shown in FIG. 3, each electrode module may have a shape similar to a T-shape. The number of electrode modules 20 included in the electrical stimulation apparatus 100 is not limited thereto. Referring to FIG. 6, in some embodiments, the electrical stimulation apparatus 100 may include a plurality of the electrode module 20. The plurality of the electrode modules 20 may be spaced apart from each other and each of the plurality of the electrode modules 20 may be connected to the frame 10. The number of electrode modules 20 may be 'n' ('n' is a natural of '2' or more).

For example, when the electrical stimulation is required at one location depending on the target effect to be provided to a user, the electrode module 20 may be '1'; when the electrical stimulation is required in a plurality of areas, the number of electrode modules 20 may be greater than or equal to '2'.

Meanwhile, because the electrical stimulation apparatus 100 according to an embodiment of the inventive concept is a device providing transcranial electrical stimulation, the current flowing in each of the plurality of microelectrodes 21 may be limited to 2 mA or less for the safety of the user. However, the inventive concept is not limited thereto.

Next, the patch 30 will be described. The patch 30 may include a sponge or hydrogel, but the material of the patch 30 is not limited thereto. The patch 30 may be formed of a material having higher impedance than the electrode module 20.

The patch 30 may be removable from the electrode module 20 and may be a replaceable consumable. When the patch 30 is attached to the electrode module 20, the one surface of the patch 30 may contact the user (e.g., head). Referring to FIG. 4, when the user wears the electrical stimulation apparatus 100, the patch 30 attached to the electrode module 20 may contact the user's head, and the patch 30 may receive current from the electrode module 20 and then may apply electrical stimulation to the user's head.

In the meantime, as described above, the patch 30 may have a size larger than the conventional patch 30 in the electrical stimulation apparatus 100 according to an embodiment of the inventive concept. However, the inventive concept is not limited thereto. For example, when the size of the conventional patch 30 is 30 mm×30 mm, the patch 30 included in the electrical stimulation apparatus 100 according to an embodiment of the inventive concept may be greater than 30 mm×30 mm, and may be, for example, 50 mm×50 mm. However, the inventive concept is not limited thereto.

Next, the processor 40 will be described. The processor may control the operation of the electrode module 20 such that the target effect is capable of being provided to the user through electrical stimulation in a state where the frame 10 is worn on the user.

In particular, because the processor 40 individually controls the operation of each of the plurality of microelectrodes 21 included in the electrode module 20, an electrical stimulation location, an electrical stimulation area, an electrical stimulation density, an electrical stimulation method, and the like may be adjusted in a state where the electrical stimulation apparatus 100 is worn by the user.

Above all, referring to FIGS. 7 to 9, it is described that the processor 40 adjusts the electrical stimulation location or the electrical stimulation area in a state where the electrical stimulation apparatus 100 is worn by the user.

Above all, referring to FIG. 7, because the electrical stimulation apparatus 100 is worn on the user and the relative connection relation between the frame 10 and the electrode module 20 is determined in advance, in some embodiments, where the electrode module 20 is fixed on the user may be determined by receiving and analyzing an image indicating that the electrical stimulation apparatus 100 is worn on the user, through a communication unit (not illustrated).

However, information about where the electrode module 20 is fixed on the user does not need to be generated by the electrical stimulation apparatus 100, and the electrical stimulation apparatus 100 may receive the corresponding information from the outside through the communication unit (not illustrated). However, the inventive concept is not limited thereto.

In addition, a target region 'X' of the user may be determined depending on the target effect of the electrical stimulation apparatus 100, and the target region 'X' may be grasped by receiving and analyzing an image indicating that the electrical stimulation apparatus 100 is worn on the user through the communication unit (not illustrated). However, the inventive concept is not limited thereto. The electrical stimulation apparatus 100 may receive the corresponding information from the outside through the communication unit (not illustrated).

Next, referring to FIG. 8, the processor 40 may adjust the electrical stimulation location or the electrical stimulation area so as to apply electrical stimulation to the target region 'X' by controlling whether to operate each of the plurality of microelectrodes 21 in a state where the frame 10 is worn on the user. In particular, the processor 40 may operate at least one microelectrode 21 facing the target region 'X' of the user in a state where the frame 10 is worn on the user.

However, because the electrical stimulation is generally applied to an area wider than the target region when the electrical stimulation is applied to the target region, the processor 40 may operate at least one microelectrode 21 facing the predetermined range from the target region of the user in a state where the frame 10 is worn on the user. For example, when the default stimulation unit is 30 mm×30 mm, the electrical stimulation area by the electrical stimulation apparatus 100 may be adjusted by setting the predetermined range to 30 mm×30 mm.

In the meantime, referring to FIG. 8, because the electrode surface of the electrode module 20 in the electrical stimulation apparatus 100 according to an embodiment of the inventive concept is greater than the size of the reference electrical stimulation, while the electrical stimulation is applied to the user by the electrical stimulation apparatus 100, at least one microelectrode 21 may not be operated by the processor 40 and only the part of the microelectrodes 21 may be operated.

Herein, the adjusting of the electrical stimulation location or the electrical stimulation area may be described as adjusting the stimulation center of the electrode module 20. In particular, the processor 40 may adjust the electrical stimulation location or the electrical stimulation area, by controlling the operation of the electrode module 20 such that the stimulation center of the electrode module 20 is adjusted in a state where the frame 10 is worn on the user.

Herein, the stimulation center of the electrode module 20 may be the center of the electrical stimulation generated by at least one microelectrode 21, which is used for the electrical stimulation, from among the plurality of microelectrodes 21. For example, referring to FIG. 8, the location of the microelectrode 21 or the electrode module 20 that faces the target region 'X' of the user may be the stimulation center of the electrode module 20.

That is, the adjusting of the electrical stimulation location or the electrical stimulation area may be to adjust the stimulation center of the electrode module 20 such that the electrical stimulation occurs in an area of the predetermined range along the stimulation center of the electrode module 20.

Meanwhile, in accordance with the electrical stimulation apparatus 100 according to an embodiment of the inventive concept, the stimulation center of the electrode module 20 may be adjusted in a state where the electrical stimulation apparatus 100 is worn on the user. For example, referring to FIGS. 8 and 9, while the electrical stimulation by the electrical stimulation apparatus 100 is applied, the target region of the user may be changed (X→Y). In this case, the processor 40 may control the operation of the electrode module 20 such that the stimulation center of the electrode module 20 is changed from a first location 'X' to a second location 'Y' within the electrode module 20. As such, the electrical stimulation location or the electrical stimulation area may be also adjusted in a state where the electrical stimulation apparatus 100 is worn on the user.

In particular, the processor 40 may continue to operate at least part of the plurality of microelectrodes 21 such that the stimulation center of the electrode module 20 is changed from the first location 'X' to the second location 'Y' within the electrode module 20. Referring to FIGS. 8 and 9, about two microelectrodes 21 may continue the operation even though the stimulation center of the electrode module 20 is changed.

In addition, the processor 40 may interrupt the operation of at least part of the plurality of microelectrodes 21 such that the stimulation center of the electrode module 20 is changed from the first location 'X' to the second location 'Y' within the electrode module 20. Referring to FIGS. 8 and 9, the part of the microelectrodes 21 may stop the operation due to the change of the stimulation center of the electrode module 20.

Next, it is described with reference to FIG. 10 that the processor 40 adjusts the electrical stimulation density in a state where the electrical stimulation apparatus 100 is worn on the user.

The processor 40 may control the polarity of at least one microelectrode 21 used for the electrical stimulation among the plurality of microelectrodes 21, in a state where the frame 10 is worn on the user. For example, the electrical stimulation density may be high or low such that the target effect is provided to the user through the electrical stimulation. In this case, the processor 40 may adjust the electrical stimulation density by changing the polarity distribution of the microelectrode 21.

For example, referring to FIG. 10, the polarity of at least one microelectrode 21 used for the electrical stimulation among the plurality of microelectrodes 21 may be adjusted to a cathode or an anode. For example, the microelectrode 21 corresponding to the target region may be adjusted to the cathode, and the microelectrode 21 surrounding the cathode may be adjusted to the anode. However, the inventive concept is not limited thereto.

In addition, the processor 40 may adjust the electrical stimulation method in a state where the electrical stimulation apparatus 100 is worn by the user. For example, the electrical stimulation method may be one of electrical stimulation strength, electrical stimulation interval, electrical stimulation type (e.g., DC electrical stimulation, AC electrical stimulation, or the like), and the like. However, the inventive concept is not limited thereto.

In accordance with the electrical stimulation apparatus 100 according to an embodiment of the inventive concept, for the purpose of providing a user with a target effect in a state where the user wears the electrical stimulation apparatus 100, the electrical stimulation location or the electrical stimulation density may be adjusted through the individual control of the microelectrode 21. That is, because the electrical stimulation apparatus 100 does not need to be removed to adjust the electrical stimulation location or electrical stimulation density when the electrical stimulation apparatus 100 according to an embodiment is used, it is possible to maximize the convenience of the user and to provide the target effect to the user through electrical stimulation.

Hereinafter, referring to FIGS. 11A and 11B, the electrical stimulation apparatus 100 according to the second embodiment of the inventive concept will be described. However, the difference from the electrical stimulation apparatus 100 according to the first embodiment of the inventive concept will be described mainly Referring to FIGS. 11A and 11B, the drawing illustrating a schematic configuration of the electrical stimulation apparatus 100 according to the second embodiment of the inventive concept is illustrated.

Referring to FIGS. 11A and 11B, the frame 10 may be worn by a user in an adhesive manner. To this end, for example, the first surface 10a of the frame 10 may include, but is not limited to, an adhesive. In addition, because the relative connection relation between the frame 10 and the electrode module 20 is also determined in advance in the electrical stimulation apparatus 100 according to an embodiment of the inventive concept, the electrical stimulation apparatus 100 according to an embodiment of the inventive concept may have the difference from the electrical stimulation apparatus 100 according to the first embodiment in the wearing method, and the technical features of the electrical stimulation apparatus 100 according to the first embodiment may be applied as it is.

Hereinafter, referring to FIGS. 12 and 13A to 13D, the electrical stimulation apparatus 100 according to the third embodiment of the inventive concept will be described. However, the difference from the first embodiment of the inventive concept will be described mainly. Referring to FIG. 12, the electrode module 20 of the electrical stimulation apparatus 100 according to the third embodiment of the inventive concept is illustrated. Referring to 13A to 13D, a view for describing the operation of the electrical stimulation apparatus 100 is illustrated.

Referring to FIG. 12, the electrode module 20 may be nonuniformly divided such that the plurality of microelectrodes 21 may be arranged nonuniformly, and the plurality of microelectrodes 21 may be arranged nonuniformly.

For example, each of the plurality of microelectrodes 21 may include the surface of the microelectrode 21. The size of one of the surfaces of the plurality of microelectrodes 21 may be different from the size of another of the surfaces of the plurality of microelectrodes 21. For example, as shown in FIG. 12, each microelectrode of the plurality of microelectrodes 21 has a shape similar to a rectangle, the plurality of microelectrodes include first microelectrodes, each of which has a shape similar to a square (e.g., 21a, 21c, 21g, and 21i), and second microelectrodes, each of which has a shape similar to a non-square rectangle (e.g., 21b, 21d, 21e, 21f, and 21h).

Furthermore, the density of the microelectrode 21 positioned in the center area of the electrode module 20 may different from the density of the microelectrode 21 positioned in the outer area of the electrode module 20. For example, because the single microelectrode 21 is positioned in the wide area in the center area of the electrode module 20, the density of the microelectrode 21 may be low. Because the single microelectrode 21 is positioned in the narrow area in the outer area of the electrode module 20, the density of the microelectrode 21 may be high. However, the inventive concept is not limited thereto.

Because the plurality of microelectrodes 21 are nonuniformly arranged in the electrical stimulation apparatus 100 according to an embodiment of the inventive concept, referring to 13A to 13D, the electrical stimulation location may be adjusted effectively. In particular, the processor 40 may control the operation of the electrode module 20 in units of a predetermined set of microelectrodes 21. Herein, the predetermined set of microelectrodes 21 may include two or more microelectrodes 21, which are arranged to be adjacent thereto, from among the plurality of microelectrodes 21.

For example, in the electrical stimulation apparatus 100 according to an embodiment of the inventive concept, the number of sets of the microelectrodes 21 may be four. Each of the sets of the microelectrodes 21 may have the same size of an electrode surface. However, the inventive concept is not limited thereto.

(a) 21a, 21b, 21d, 21e
(b) 21b, 21c, 21e, 21f
(c) 21d, 21e, 21g, 21f
(d) 21e, 21f, 21h, 21i

Referring to 13A to 13D, while the electrical stimulation is applied to the user by the electrical stimulation apparatus 100, at least the same single microelectrode 21 21e may be always operated by the processor 40. Accordingly, in accordance with the electrical stimulation apparatus 100 according to an embodiment of the inventive concept, because at least the same single microelectrode 21 is always operated, the electrical stimulation apparatus 100 may be controlled efficiently.

Hereinafter, the embodiment associated with a method for controlling the electrical stimulation apparatus 100 of the inventive concept will be described in detail with reference to accompanying drawings. However, the content overlapping with that described in the electrical stimulation apparatus 100 of the inventive concept will be described briefly.

Hereinafter, the method for controlling the electrical stimulation apparatus 100 according to the first embodiment of the inventive concept will be described with reference to FIGS. 1 and 14 to 16. FIG. 14 is a flowchart of a method for controlling the electrical stimulation apparatus 100, according to the first embodiment of the inventive concept. FIG. 15 is a flowchart of operation S10 in FIG. 14. FIG. 16 is a view for describing an execution subject of a method for controlling the electrical stimulation apparatus 100, according to the first embodiment of the inventive concept.

According to an embodiment of the inventive concept, the control method of the electrical stimulation apparatus 100 refers to a method of controlling the electrical stimulation apparatus 100 in a state where the electrical stimulation apparatus 100 including the frame 10 worn on a user, the electrode module 20 including the plurality of microelectrodes 21 is worn on the user, and the patch 30 of which one surface of is connected to the frame and of which the other surface contacts the user.

Referring to FIGS. 1 and 14, in operation S10, the electrical stimulation apparatus 100 may determine that the electrical stimulation apparatus 100 is worn on the user.

Operation S10 may be an operation of obtaining information about the user and the electrical stimulation apparatus 100. Referring to FIG. 15, operation S10 of determining the state where the electrical stimulation apparatus 100 is worn on the user may include operation S11 in which the electrical stimulation apparatus 100 identifies a location at which the frame 10 is fixed on the user and the target region of the user and operation S12 in which the electrical stimulation apparatus 100 calculates the location of the electrode module 20 on the user based on the mutual connection relation between the frame 10 and the electrode module 20.

Herein, operation S11 in which the electrical stimulation apparatus 100 identifies the location at which the frame 10 is fixed on the user and the target region of the user may be an operation of analyzing an image indicating that a state where the electrical stimulation apparatus 100 is worn on the user. Referring to FIG. 16, the image indicating that a state where the electrical stimulation apparatus 100 is worn on the user may be captured from the smart device 200 with a camera function, and the captured image may be transmitted from the smart device 200 to the electrical stimulation apparatus 100. Moreover, the electrical stimulation apparatus 100 may identify the frame 10 and the target region of the user, to which the electrical stimulation needs to be applied, from the transmitted image.

Furthermore, the location of the electrode module 20 on the user may be calculated based on the mutual connection relation between the frame 10 and the electrode module 20.

Next, referring to FIG. 14, in operation S20, the electrical stimulation apparatus 100 may control the operation of the electrode module 20 based on the determined result such that the target effect is capable of being provided to the user through electrical stimulation in a state where the frame 10 is worn on the user.

For example, operation S20 of controlling the operation of the electrode module 20 based on the determined result may be an operation of adjusting the electrical stimulation location or the electrical stimulation area by controlling whether to operate each of the plurality of microelectrodes 21 in a state where the frame 10 is worn on the user, in consideration of the target region of the user and the location of the electrode module 20 on the user.

Herein, the electrical stimulation apparatus 100 may operate at least one microelectrode 21 facing the target region of the user in a state where the frame 10 is worn on the user or may operate at least one microelectrode 21 facing the predetermined range from the target region of the user in a state where the frame 10 is worn on the user.

In the meantime, operation S20 of controlling the operation of the electrode module 20 based on the determined result may be an operation of adjusting the electrical stimulation location by controlling the operation of the electrode module 20 such that the stimulation center of the electrode module 20 is capable of being adjusted in a state where the frame 10 is worn on the user, based on the determined result. Herein, the stimulation center of the electrode module 20 may be the center of the electrical stimulation occurring by at least one microelectrode 21 used for the electrical stimulation among the plurality of microelectrodes 21.

In addition, operation S20 of controlling the operation of the electrode module 20 based on the determined result may be an operation of adjusting the electrical stimulation density by controlling the polarity of at least one microelectrode 21 used for electrical stimulation among the plurality of microelectrodes 21, based on the determined result. Herein, the controlling of the polarity of microelectrode 21 may be determining that the polarity of the microelectrode 21 is one of a cathode or an anode.

The steps of a method or algorithm described in connection with the embodiments of the inventive concept may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form known in the art to which the inventive concept pertains.

Hereinafter, referring to FIG. 17, a controlling method of the electrical stimulation apparatus 100 according to the second embodiment of the inventive concept will be described. However, the difference from the controlling method of the electrical stimulation apparatus 100 according to the first embodiment of the inventive concept will be described mainly. Referring to FIG. 17, a view for describing the execution subject of a method for controlling the electrical stimulation apparatus 100 according to the second embodiment of the inventive concept is illustrated.

Referring to FIG. 17, even though the execution subject in the method for controlling the electrical stimulation apparatus 100 according to the first embodiment of the inventive concept is the electrical stimulation apparatus 100, the execution subject in the method for controlling the electrical stimulation apparatus 100 according to the second embodiment of the inventive concept may be a server 300.

For example, the server 300 may receive information from the smart device 200 and then may analyze the information. The server 300 may transmit a control signal for controlling the operation of the electrode module 20, to the electrical stimulation apparatus 100 to control the operation of the electrode module 20.

In the meantime, the technical features of the electrical stimulation apparatus 100 according to an embodiment of the inventive concept and the controlling method thereof may be applied to a brain-wave measuring device and the controlling method thereof as it is.

For example, a brain-wave measuring device may include the frame 10 worn on the user, the electrode module 20 including the plurality of microelectrodes 21 covered by the single patch 30, and the processor 40 controlling the operation of the electrode module 20 such that the brain-wave is capable of being measured in a state where the frame 10 is worn on the user. One surface of the electrode module 20 is connected to the frame 10, and the other surface faces the user while being covered by the single patch 30.

In addition, the processor 40 may adjust the measurement location or the measurement area to measure the brain-wave at the target region 'X' by controlling whether to operate each of the plurality of microelectrodes 21 in a state where the frame 10 is worn on the user. In particular, the processor 40 may operate at least one microelectrode 21 facing the target region 'X' of the user in a state where the frame 10 is worn on the user.

Although embodiments of the inventive concept have been described herein with reference to accompanying drawings, it should be understood by those skilled in the art that the inventive concept may be embodied in other specific forms without departing from the spirit or essential features thereof. Therefore, it should be understood that the above embodiments are not limiting, but illustrative.

For the purpose of providing a user with a target effect in a state where the user wears an electrical stimulation apparatus, the electrical stimulation location may be adjusted or the electrical stimulation density may be adjusted, through the individual control of a microelectrode. That is, because the electrical stimulation apparatus does not need to be removed to adjust the electrical stimulation location or the electrical stimulation density when the electrical stimulation apparatus according to the inventive concept is used, it is possible to maximize the convenience of the user and to provide the target effect to the user through electrical stimulation.

The effects of the present inventive concept are not limited to the aforementioned effects, and other effects not mentioned herein will be clearly understood from the following description by those skilled in the art to which the inventive concept pertains.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. An electrical stimulation apparatus comprising:
a frame configured to be worn by a user;
an electrode module having a first shape similar to a T-shape and including a plurality of microelectrodes,
wherein each microelectrode of the plurality of microelectrodes has a second shape similar to a rectangle,
wherein the plurality of microelectrodes include first microelectrodes, each of which has a third shape similar to a square, and second microelectrodes, each of which has a fourth shape similar to a non-square rectangle,
wherein the plurality of microelectrodes are arranged in a grid shape and are covered by a single patch,
wherein the plurality of microelectrodes are separated each other by a non-conductive material disposed between the plurality of microelectrodes, and
wherein one surface of the electrode module is connected to the frame and the other surface faces the user while being covered by the single patch; and
a processor configured to control an operation of the electrode module such that a target effect is capable of being provided to the user through electrical stimulation in a state where the frame is worn on the user.

2. The electrical stimulation apparatus of claim 1, wherein the processor is configured to:
adjust an electrical stimulation location by controlling whether to operate each of the plurality of microelectrodes, in the state where the frame is worn on the user.

3. The electrical stimulation apparatus of claim 2, wherein the processor is configured to:
operate at least one microelectrode facing a target region of the user, in the state where the frame is worn on the user.

4. The electrical stimulation apparatus of claim 2, wherein the processor is configured to:
operate at least one microelectrode facing a predetermined range from a target region of the user, in the state where the frame is worn on the user.

5. The electrical stimulation apparatus of claim 1, wherein the processor is configured to:
adjust an electrical stimulation location by controlling the operation of the electrode module such that a stimulation center of the electrode module is capable of being adjusted in the state where the frame is worn on the user.

6. The electrical stimulation apparatus of claim 5, wherein the stimulation center of the electrode module is a center of the electrical stimulation generated by at least one microelectrode used for the electrical stimulation among the plurality of microelectrodes.

7. The electrical stimulation apparatus of claim 1, wherein at least one microelectrode is not operated by the processor, while the electrical stimulation is applied to the user by the electrical stimulation apparatus.

8. The electrical stimulation apparatus of claim 1, wherein the processor is configured to:
adjust electrical stimulation density by controlling a polarity of at least one microelectrode used for the electrical stimulation among the plurality of microelectrodes in the state where the frame is worn on the user.

9. The electrical stimulation apparatus of claim 1, wherein each of the plurality of microelectrodes includes a microelectrode surface, and
wherein a size of one microelectrode surface of the plurality of microelectrode surfaces is different from a size of another microelectrode surface of the plurality of microelectrode surfaces.

10. The electrical stimulation apparatus of claim 9, wherein at least one microelectrode is always operated by the processor, while the electrical stimulation is applied to the user by the electrical stimulation apparatus.

11. The electrical stimulation apparatus of claim 9, wherein the processor is configured to:
control the operation of the electrode module in units of a predetermined set of microelectrodes, and
wherein the predetermined set of microelectrodes includes two or more microelectrodes, which are arranged adjacent to each other, from among the plurality of microelectrodes.

12. The electrical stimulation apparatus of claim 1, wherein the electrical stimulation apparatus includes a plurality of electrode modules, and
wherein the plurality of electrode modules are spaced apart from each other and each of the plurality of electrode modules is connected to the frame.

13. The electrical stimulation apparatus of claim 1, wherein the frame is worn on the user by a structural feature of the frame or is worn on the user in an adhesive manner.

14. The electrical stimulation apparatus of claim 1, wherein the patch includes a sponge or hydrogel.

15. The electrical stimulation apparatus of claim 14, further comprising:
a single patch that covers the plurality of microelectrodes included in the electrode module,
wherein one surface of the patch contacts the user.

16. The electrical stimulation apparatus of claim 1, wherein the frame is worn on a head of the user.

17. The electrical stimulation apparatus of claim 1, wherein current flowing into each of the plurality of microelectrodes of the electrode module is limited to 2 mA or less.

18. The electrical stimulation apparatus of claim 1, wherein the target effect is a treatment for a specific mental illness.

19. An electrical stimulation apparatus comprising:
a frame configured to be worn by a user;
an electrode module having a first shape similar to a T-shape and including a plurality of microelectrodes,
wherein each microelectrode of the plurality of microelectrodes has a second shape similar to a rectangle,
wherein the plurality of microelectrodes include first microelectrodes, each of which has a third shape similar to a square, and second microelectrodes, each of which has a fourth shape similar to a non-square rectangle,
wherein the plurality of microelectrodes are arranged in a grid shape and are covered by a single patch,
wherein one surface of the electrode module is connected to the frame and the other surface faces the user while being covered by the single patch; and
a processor configured to control an operation of the electrode module such that a target effect is capable of being provided to a target region of the user through electrical stimulation in a state where the frame is worn on the user, wherein the processor is further configured to control a first set of microelectrodes, which are directly adjacent to each other, to apply a first electrical stimulation to a first target region by the microelectrodes included in the first set, during the target region is the first target region, and configured to control a second set of microelectrodes, which are directly adjacent to each other, to apply a second electrical stimulation to a second target region by the microelectrodes included in the second set, during the target region is the second target region, and wherein the first set of microelectrodes and the second set of microelectrodes have one or more overlapped microelectrodes, such that the one or more overlapped microelectrodes are configured to apply a part of the first electrical stimulation and also apply a part of the second electrical stimulation.

* * * * *